United States Patent [19]

Tubo et al.

[11] Patent Number: 5,040,677
[45] Date of Patent: Aug. 20, 1991

[54] CONTAINER FOR STORAGE AND DISTRIBUTION OF A SKIN WOUND DRESSING

[75] Inventors: Ross A. Tubo, Quincy; Richard Odessey, Newton Lower Falls, both of Mass.

[73] Assignee: Biosurface Technology, Inc., Cambridge, Mass.

[21] Appl. No.: 532,965

[22] Filed: Jun. 4, 1990

[51] Int. Cl.$^5$ .............................................. B65D 85/50
[52] U.S. Cl. ................................ 206/440; 435/240.23; 623/11
[58] Field of Search ...................... 206/438–441, 206/484, 632, 633, 362, 363; 128/156; 435/240.23, 240.25; 623/11

[56] References Cited

U.S. PATENT DOCUMENTS

| | | | |
|---|---|---|---|
| 2,649,392 | 8/1953 | Marshall | 206/633 |
| 2,990,948 | 7/1961 | Zackheim | 206/633 |
| 3,403,776 | 10/1968 | Denny | 206/363 |
| 3,717,244 | 2/1973 | Smith | 206/484 |
| 3,903,882 | 9/1975 | Augurt | 128/156 |
| 4,016,036 | 4/1977 | Green et al. | 435/240.23 |
| 4,304,866 | 12/1981 | Green et al. | 623/11 |
| 4,456,687 | 6/1984 | Green | 435/240.23 |
| 4,557,381 | 12/1985 | Whitney | 206/438 |
| 4,630,448 | 12/1986 | Bilstad et al. | 62/60 |
| 4,681,839 | 7/1987 | Swartz | 435/260 |
| 4,687,476 | 8/1987 | Pailin | 206/484 |

FOREIGN PATENT DOCUMENTS

| | | | |
|---|---|---|---|
| 2136166 | 9/1972 | Fed. Rep. of Germany | 206/484 |
| 2436084 | 5/1980 | France | 206/438 |
| 8603976 | 7/1986 | PCT Int'l Appl. | 206/363 |

OTHER PUBLICATIONS

H. Green, "Terminal Differentiation of Cultured Human Epidermal Cells", Cell, vol. 11, 405–416, Jun. 1977.
R. Blondet, M. A. Gibert-Thevenin, C. Pierre & A. Ehrsam, "Skin Preservation by Programmed Freezing", British Journal of Plastic Surgery, vol. 35, pp. 530–536 (1982).
S. Randolph May, R. Guttman, & J. Wainwright, "Cryopreservation of Skin Using an Insulated Heat Sink Box Stored at −70° C.", Cryobiology, vol. 22, pp. 205–214 (1985).
BioSurface Technology, Inc., "Epithelial Cell Culturing Service", Mar. 1988.
BioSurface Technology, Inc., "Cultured Autograft Service Orientation Manual", (1988).
F. Kasten & D. Yip, "A Simple Device and Procedure for Successful Freezing of Cells in Liquid Nitrogen Vapor", Methods in Cell Biology, vol. 14, 165–179 (1976).

Primary Examiner—Jimmy G. Foster
Attorney, Agent, or Firm—Testa, Hurwitz & Thibeault

[57] ABSTRACT

Disclosed is a container for the storage and distribution of a cultured epithelial, generally planar, living, skin wound dressing that allows the dressing to be gently removed by lifting perpendicular to a support surface in the container. The design minimizes handling of the graft dressing thereby promoting cell viability.

14 Claims, 3 Drawing Sheets

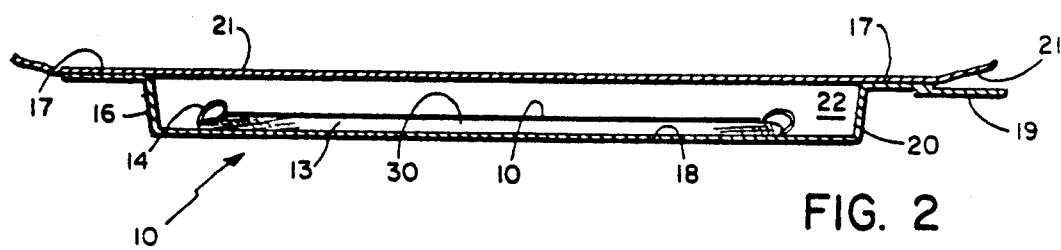
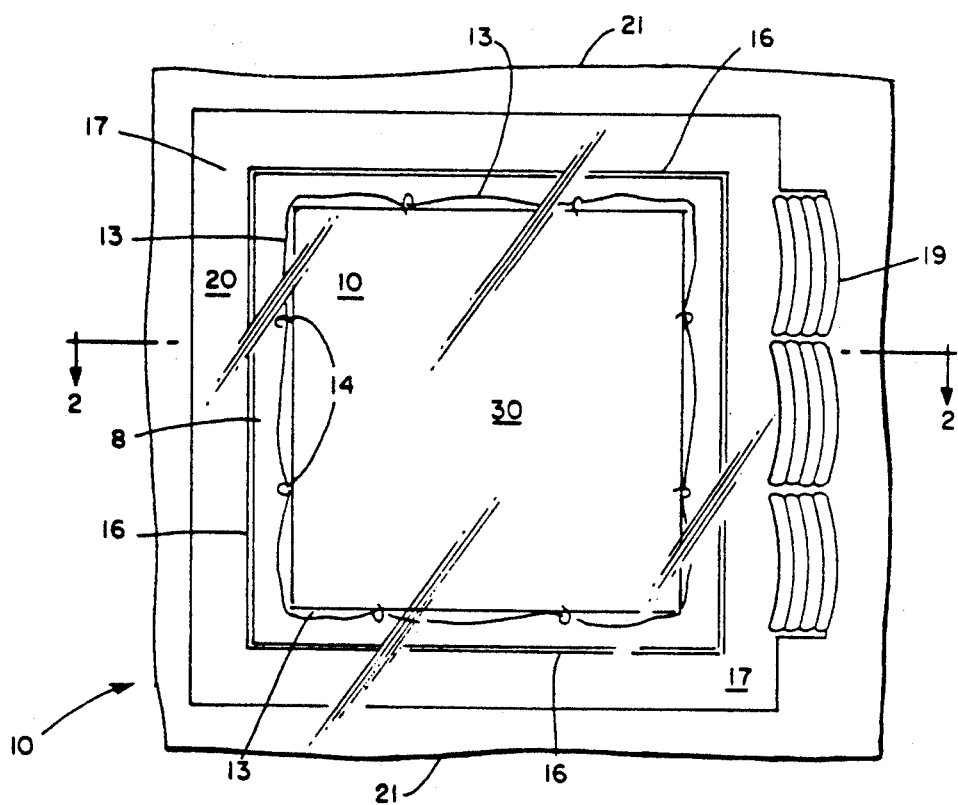

CONTAINER FOR STORAGE AND DISTRIBUTION OF A SKIN WOUND DRESSING

BACKGROUND OF THE INVENTION

This invention relates to the field of tissue storage and distribution.

It has been a priority in the medical community to develop a skin wound dressing which will encourage new growth while preventing fluid loss and infection following skin wounds from burns, ulceration, or surgical excision. Traditional bandages and dressings fail to protect large-scale wounds adequately, therefore various alternatives have been developed. Among these are split- and full-thickness grafts of cadaver or porcine skin, and human allografts and autografts. Most have proved unsatisfactory since all but autografts eventually are rejected by the body in the absence of immunosuppressive therapy. Autografts are useful in small areas, but use of conventional autografting technique is not practical for massive burn injury involving large body surface areas. Cultured sheets of epithelial cells for use as skin wound dressings are now available commercially from Biosurface Technology, Inc. of Cambridge, Mass.

Currently, cultured grafts are delivered directly to the operating room at the burn center or hospital for application to the patient. Each graft package consists of a layer of cultured epithelium attached with surgical clips to a backing of petrolatum gauze. Each cultured graft is approximately 25 cm$^2$ in size and is individually packaged in a shallow dish containing a small amount of serum-free, sodium bicarbonate buffered medium which contains antibiotics. Multiple dishes containing the grafts are shipped in a sterilized gas-tight container. The transport container must be gas tight, since the sodium bicarbonate buffered medium requires 10% $CO_2$ for maintenance of proper pH.

Problems that have been encountered with the current transport system include spillage of medium from shallow tissue culture dishes into the sterilized transport box, loss of the gas tight nature of the box during transit, resulting in grafts being maintained in medium at basic pH for an unknown period of time, and detachment of the epithelium from the vaseline gauze backing, due to shear forces of medium sloshing around during transit.

The use of these grafts as skin wound dressings also presents other practical difficulties. The tensile strength of the grafts is such that they often cannot support their own weight and tear if suspended by an edge. For this reason, the grafts are attached to gauze to allow easier handling. Once a graft has folded over upon itself it is very difficult to restore to its original planar configuration, and essentially impossible without the gauze backing. Handling of the grafts should be kept to a minimum since handling causes a significant, measurable reduction in cell viability.

The object of this invention is to provide a specially designed container for storage and distribution of a skin wound dressing which allows a minimum of handling and easy removal so that maximal viability of the dressing is maintained prior to application to skin wounds arising from burns and other injuries. The object is achieved by the provision and use of a gas-tight sealable container for individual grafts. The containers, once sealed, are gas-tight and spill proof. In addition, since the grafts are stored with minimal air space, shear forces that tear the graft away from its backing are reduced.

SUMMARY OF THE INVENTION

The invention is embodied as an article of manufacture useful in the storage and distribution of a skin wound dressing comprising a housing or package containing a cultured epithelial sheet. The housing defines a support surface for a planar, cohesive sheet of cultured epithelial cells capable of replication upon application to a skin wound. The housing is sealed with a cover to define an enclosed space for the epithelial cell sheet. The seal can be broken and the cover removed so that the planar sheet of epithelial cells can be removed intact and with minimal mechanical stress by lifting to peel the sheet away perpendicular to the support surface. The housing may contain an epithelial cell storage medium, which may be saline or a culture medium, or it may contain a cryoprotectant. The planar sheet of epithelial cells typically is less than about 10 cells thick, and is partially differentiated. The sheet may be attached releasably to a backing sheet or substrate disposed between the planar sheet of cells and the support surface of the container. The cells are preferably keratinocytes, and the backing sheet is preferably petrolatum gauze. The container may have side walls and an integral gripping tab for manually holding the container and facilitating removal of the cover.

BRIEF DESCRIPTION OF THE DRAWINGS

For a fuller understanding of the nature, objects, and features of the invention, reference should be made to the following detailed description and accompanying drawings, wherein:

FIG. 1 is a top plan view of the article of manufacture of the invention showing an epithelial sheet enclosed within a housing;

FIG. 2 is a cross-sectional view of the product of FIG. 1 taken at lines 2—2;

Like reference characters in the respective drawn figures indicate corresponding parts.

DESCRIPTION

Figure 3:
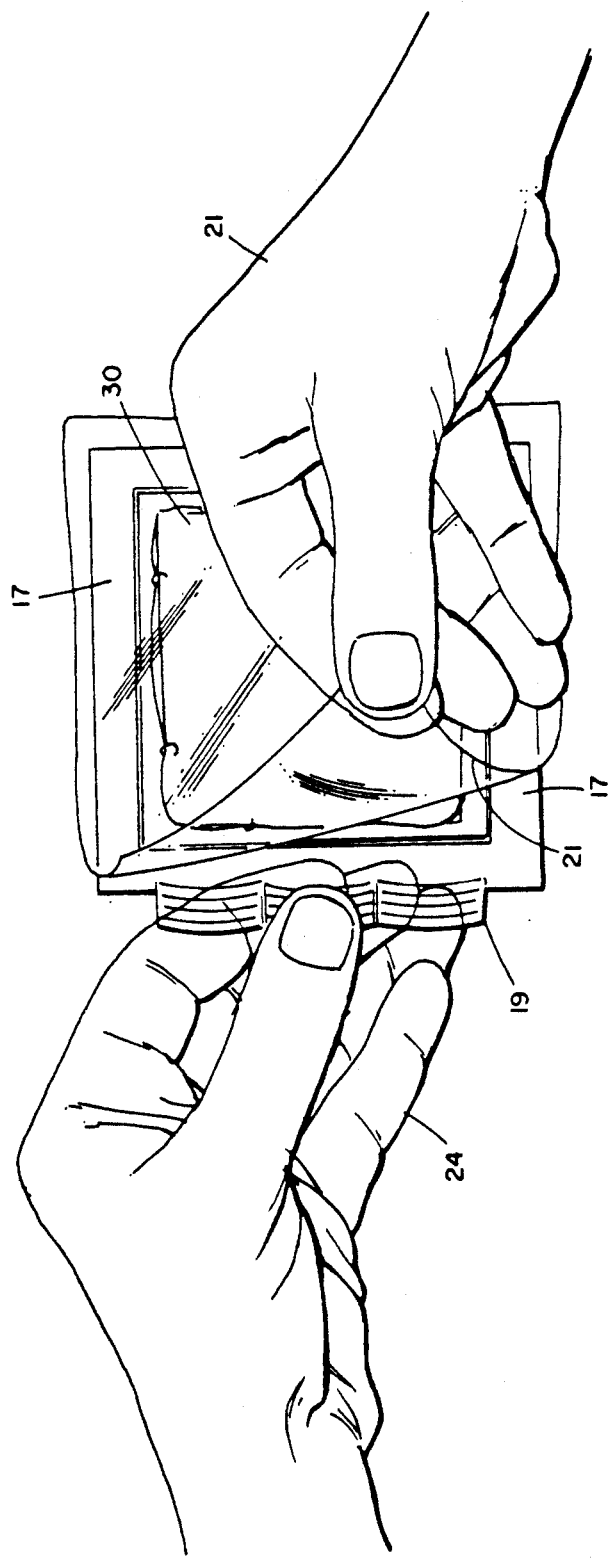
FIG. 3 illustrates the manual removal of the cover from the housing of the product of the invention.

This invention relates to a container for the storage and distribution of a skin wound dressing. The container facilitates storage and subsequent transport and application of intact, living, cultured epithelial cell sheets from a central manufacturing facility to the site of surgery to treat skin wounds arising from burns and other injuries.

Cultured human epithelial cell sheets can function as permanent autograft material for repair of skin wounds. As temporary allograft material, the sheets are also a highly effective burn wound dressing and can Promote healing of chronic skin ulcers and split-thickness graft donor sites. The sheets may be produced using a culture system developed by Rheinwald and Green, wherein epithelial cells divide rapidly on the surface of tissue culture dishes or flasks and ultimately form a confluent, modestly stratified sheet of tightly interconnected cells. Confluent epithelial cell cultures can be released as coherent cell sheets by treatment with an enzyme, such as dispase, then stapled to gauze impregnated with petroleum jelly such as Vaseline ®, transported to the operating room, and applied to the patient. For a detailed disclosure of methods for producing the cultured epithelial sheets, see U.S. Pat. No. 4,016,036, 4,304,866, and 4,456,687, the disclosures of which are incorporated herein by reference.

The cell cultures are used to prepare grafts within 2 days of reaching confluence. The supernatant medium is aspirated from the culture flask and the cell sheet is cut to produce two equal areas. Forty ml of Dispase II (Boehringer Mannheim) at a final concentration of 2.5 mg/ml (approximately 1.2U/ml) is added to the flask, which is then put into a sterile plastic bag and incubated at 37° C. in a humidified atmosphere of 10% $CO_2$ in air. The cultured grafts comprise a layered sheet of epithelial cells less than about 10 cells thick. The sheet typically is moderately stratified into partially differentiated layers including a superficial layer and an underlying germinative layer that ultimately will be placed in contact with the surface of the wound.

FIGS. 1 and 2 illustrate a package 10 comprising a housing 20 and a cover 21 which together define a space 22 containing a skin wound dressing designated generally at 30. The housing 20 comprises side walls 16 connected at their top edge to a sealing portion 17 and at their bottom edge by a dressing support surface 18. A gripping tab 19 is integral with and extends outwardly from side wall 16. The cover 21 is sealed to the housing 20 at sealing portions 17 to provide the liquid-impervious space 22 about the wound dressing 30. The cover 21 may be attached to the sealing portion 17 by heat, adhesive, or other means known in the art. The space 22 may contain saline or a culture medium, either or both of which may be supplemented with one or more cryoprotectants.

Skin wound dressing 30 comprises a cultured, cohesive sheet of epithelial cells 10 disposed upon an adhesive substrate sheet or backing 13, so that the germinative layer of the graft 10 is facing upwards toward the cover 21. Graft 10 is releasably attached to substrate sheet 13 by clips 14. Substrate sheet 13 preferably comprises petrolatum gauze. It facilitates manipulation of graft 10 prior to application to a skin wound and thereafter serves as a removable dressing overlying the graft 10 on the skin wound.

Housing 20 may be fabricated, for example, by vacuum forming a sheet of thermoplastic material, Preferably an optically clear plastic. Polyethylene terephthalate glycol is the currently preferred material. Cover 21 most preferably comprises polyolefin, and is sealed to the housing by means of a heat sealable resin. The package is sterilized Prior to use by, for example, exposure to 2.5 to 3.0 megarads of gamma radiation. The package may be used for storage or transport of frozen or non-frozen epithelial cell sheets. Details of the currently preferred freezing and thawing protocols are disclosed in copending U.S. application Ser. No. 07/533,385 filed on the same day as this application, the disclosure of which is incorporated herein by reference.

Figure 4:
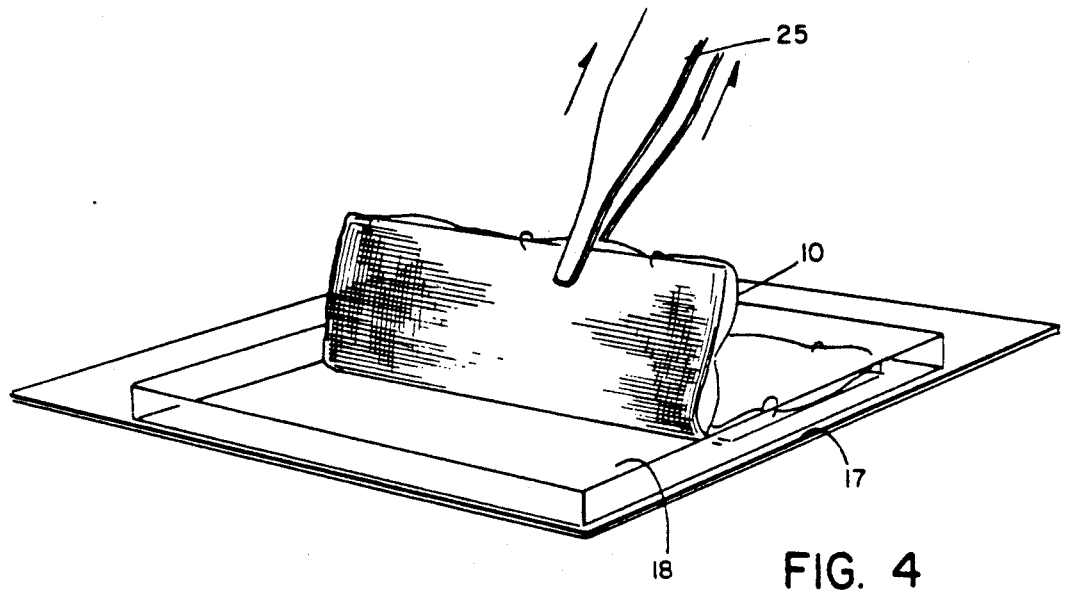
FIG. 4 illustrates the manual removal of the wound dressing from the housing.
Figure 5:
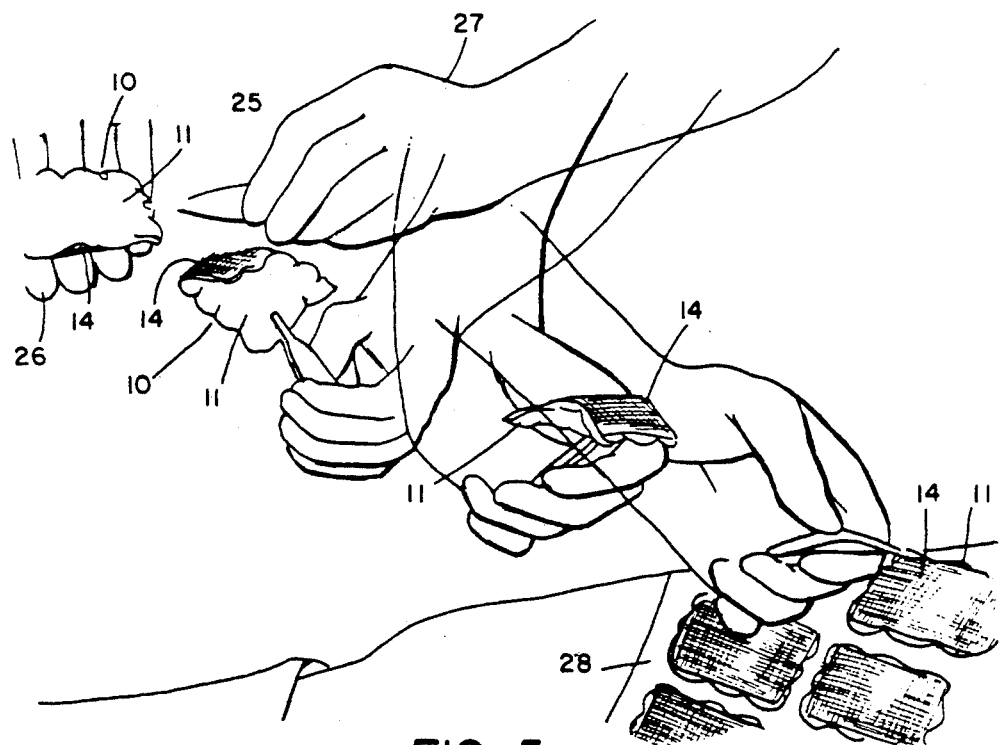
FIG. 5 illustrates the transfer of the wound dressing from the housing to the patient.

FIGS. 3, 4, and 5 illustrate use of the product of the invention. The cover 21 is grasped between the thumb and forefinger of one hand as shown. At the same time, a tab 19 is grasped and the cover 21 is removed by manually separating it from sealing engagement with sealing portions 17 of housing 20 to permit full exposure of skin wound dressing 30. As shown in FIG. 4, the dressing 30 is gently lifted upwardly perpendicularly away from or "peeled" from support surface 18 by gripping substrate sheet 13 with a forecepts 25. This mode of separation of the dressing from the package minimizes shear forces on the fragile grafts 10, and serves to maintain optimal efficacy as a graft. FIG. 5 shows topical application of a cultured graft 10. Following remove from housing 20, dressing 30 is inverted so that adhesive substrate sheet 13 is topmost and the germinative layer of sheet 10 faces downward. In this position dressing 30 is transferred to the wound, such that the germinative layer of the graft lies against the wound, protected exteriorly by adhesive substrate or backing sheet 13.

The above has been offered for illustrative purposes only, and is not intended to limit the scope of the invention of this application, which is defined in the claims below.

What is claimed is:

1. A skin wound dressing package comprising:
    a first package member defining a sealing surface;
    a second package member sealingly engaged with said sealing surface, said second package member defining, together with said first package member, a liquid impervious enclosure, one of said first and second package members comprising a dressing support surface, one of said first and second package members comprising a recess and the other comprising a sheet-like member,
    a wound dressing comprising a planar, cultured, cohesive, sheet of epithelial cells capable of replication upon application to a skin wound supported within said enclosure on said support surface in an epithelial cell storage medium; and
    means for separating said first and second package members to break said sealing engagement and to expose substantially the entire area of said planar cultured sheet, thereby to permit removal of said planar cultured sheet from said housing intact by lifting to peel said sheet away perpendicular to said support surface.

2. The package of claim 1 wherein said storage medium is saline.

3. The package of claim 1, wherein said storage medium is an epithelial cell culture medium.

4. The article of claim 1 wherein said planar sheet is less than about 10 cells thick and defines a germinative layer for contact with a skin wound.

5. The article of claim 4 further comprising an adhesive substrate sheet disposed between said support surface and said planar sheet wherein said germinative layer faces away from said substrate sheet.

6. A skin wound dressing package comprising:
    a first package member defining a sealing surface;
    a second package member sealingly engaged with said sealing surface, said second package member defining, together with said first package member, a liquid impervious enclosure, one of said first and second package members comprising a dressing support surface, one of said first and second package members comprising a recess and the other a sheet-like member, and
    a wound dressing comprising a planar, cultured, cohesive sheet of epithelial cells capable of replication upon application to a skin wound and comprising a germinative layer for contact with said skin wound facing away from said support surface, said dressing being supported within said enclosure parallel to said support surface on an adhesive substrate sheet disposed between said support surface and said cultured sheet; and means for separating said first and second package members to break said sealing engagement and to expose substantially the entire area of said planar cultured sheet, thereby to permit removal of said cultured sheet from said housing intact by lifting to peel said cultured sheet away perpendicular to said support surface.

7. The package of claim 1 or 6 comprising a cryoprotectant disposed within said enclosure wherein said sheet is frozen.

8. A skin wound dressing package comprising:
a first package member defining a sealing surface;
a second package member sealingly engaged with said sealing surface, said second package member defining, together with said first package member, a liquid impervious enclosure, one of said first and second package members comprising a dressing support service, one of said first and second package members comprising a recess and the other a sheet-like member, and
a wound dressing comprising a planar, cultured, cohesive frozen sheet of epithelial cells capable of replication after thawing upon application to a skin wound, supported within said enclosure parallel to said support service in a cryoprotectant; and means for separating said first and second package member to break said sealing engagement and to expose substantially the entire area of said planar sheet, thereby to permit removal of said planar sheet from said housing intact by lifting to peel said planar sheet away perpendicular to said support surface.

9. The package of claim 5, 6 or 8 wherein said substrate sheet is petrolatum gauze.

10. The package of claim 5, 6 or 8 wherein said substrate sheet is releasably attached to said planar sheet, whereby said substrate sheet is useful as a removable covering for said planar sheet when applied to a skin wound.

11. The package of claim 1, 6, or 8 wherein said housing and cover means comprise transparent polymeric material.

12. The package of claim 1, 6, or 8 further comprising a gripping tab integral with one of said first and second package members and extending outwardly in a plane parallel to said support surface.

13. The package of claim 1, 6 or 8 wherein said epithelial cells are keratinocytes.

14. The package of claim 1, 6 or 8 wherein said sealing surface and said cover means are adhesively bound.

* * * * *